United States Patent
Jansson et al.

(10) Patent No.: US 12,325,014 B2
(45) Date of Patent: Jun. 10, 2025

(54) LARGE PORE AGAROSE

(71) Applicant: Cytiva BioProcess R&D AB, Uppsala (SE)

(72) Inventors: David Jansson, Uppsala (SE); Jesper Hansson, Uppsala (SE); Anna Akerblom, Uppsala (SE); Emma Michaelsson, Uppsala (SE)

(73) Assignee: Cytiva BioProcess R&D AB, Uppsala (SE)

( * ) Notice: Subject to any disclaimer, the term of this patent is extended or adjusted under 35 U.S.C. 154(b) by 1034 days.

(21) Appl. No.: 17/296,684

(22) PCT Filed: Dec. 11, 2019

(86) PCT No.: PCT/EP2019/084590
§ 371 (c)(1),
(2) Date: May 25, 2021

(87) PCT Pub. No.: WO2020/126730
PCT Pub. Date: Jun. 25, 2020

(65) Prior Publication Data
US 2022/0032266 A1    Feb. 3, 2022

(30) Foreign Application Priority Data
Dec. 20, 2018   (GB) .................................... 1820806

(51) Int. Cl.
| | | |
|---|---|---|
| *B01J 20/24* | (2006.01) | |
| *B01J 20/06* | (2006.01) | |
| *B01J 20/28* | (2006.01) | |
| *B01J 20/285* | (2006.01) | |
| *C08J 3/075* | (2006.01) | |
| *C08J 3/24* | (2006.01) | |
| *C12N 7/00* | (2006.01) | |

(52) U.S. Cl.
CPC .............. *B01J 20/24* (2013.01); *B01J 20/06* (2013.01); *B01J 20/28019* (2013.01); *B01J 20/28047* (2013.01); *B01J 20/285* (2013.01); *C08J 3/075* (2013.01); *C08J 3/24* (2013.01); *C12N 7/00* (2013.01); *C08J 2305/00* (2013.01); *C08J 2305/02* (2013.01); *C12N 2710/10351* (2013.01)

(58) Field of Classification Search
CPC ...... B01J 20/24; B01J 20/06; B01J 20/28019; B01J 20/28047; B01J 20/285; C08J 3/075; C08J 3/24; C08J 2305/00; C08J 2305/02; C12N 7/00; C12N 2710/10351
USPC ...................................................... 502/404
See application file for complete search history.

(56) References Cited

U.S. PATENT DOCUMENTS

| | | |
|---|---|---|
| 6,537,793 B2 | 3/2003 | Blanche et al. |
| 2010/0099163 A1 | 4/2010 | Andersson et al. |
| 2010/0227015 A1 | 9/2010 | Cheng et al. |
| 2014/0073769 A1 | 3/2014 | Cheng et al. |

FOREIGN PATENT DOCUMENTS

| | | | |
|---|---|---|---|
| CN | 1939582 A | | 4/2007 |
| CN | 103055773 A | | 4/2013 |
| CN | 104587977 A | | 5/2015 |
| CN | 105944686 A | * | 9/2016 |
| CN | 108250495 A | * | 7/2018 |
| JP | 2007077397 A | | 3/2007 |
| JP | 2008513771 A | | 5/2008 |
| WO | WO2006033634 A1 | | 3/2006 |

OTHER PUBLICATIONS

Chinese Search Report and Office Action for CN Application No. 201980084299.4 mailed Feb. 11, 2023 (22 pages).
PCT International Search Report and Written Opinion for PCT/EP2019/084590 mailed Mar. 24, 2020 (11 pages).
Great Britain Search Report for GB Application No. 1820806.6 mailed Jun. 21, 2019 (6 pages).
JP Office Action for Japanese Patent Application No. 2021-535945, mailed Oct. 16, 2023 (9 pages).
KR Office Action in corresponding KR Application No. 10-2021-7018506, dated Nov. 8, 2024, 26 pages.

* cited by examiner

*Primary Examiner* — Edward M Johnson
(74) *Attorney, Agent, or Firm* — Eversheds-Sutherland (US) LLP

(57) ABSTRACT

The present invention relates to porous cross-linked agarose gel beads which have a low agarose content, a method for the preparation of the beads and their use in chromatographic applications. The beads are suitable for the separation/purification of biomolecules from a biological sample. Due to the high porosity of the beads, they are especially suitable for separation/isolation of larger particles, such as virus particles e.g. adeno virus.

6 Claims, No Drawings

LARGE PORE AGAROSE

CROSS REFERENCE TO RELATED APPLICATIONS

This application claims the priority benefit of PCT/EP2019/084590, filed on Dec. 11, 2019, which claims the benefit of Great Britain Application No. 1820806.6, filed on Dec. 20, 2018, the entire contents of which are incorporated by reference herein.

TECHNICAL FIELD

The present invention relates to porous cross-linked agarose gel beads which are suitable for separation/purification of biological samples. The particles are particularly suitable for the separation of virus particles, such as adenovirus, from a biological sample. The invention further relates to a method for the preparation of the beads and their use in separation/purification applications.

BACKGROUND

Agarose is a natural polysaccharide extracted from red algae. It is one of the two principal components of agar and is purified from agar by removing the other component, agaropectin. In aqueous solution at low temperatures agarose forms a hydrogel which forms a meshwork that contains pores. The pore size depends on the concentration of agarose added. Agarose gel, typically in the form of spherical beads, has been used as chromatography medium in purification applications since 1960s, and a wide range of different agaroses of varying molecular weights and properties are commercially available. Agarose gel has many advantageous characteristics, such as high hydrophilicity, high porosity, and hydroxyl groups available for functionalization. Agarose is frequently used as a base matrix e.g. in affinity chromatography, hydrophobic interaction chromatography (HIC), reverse phase chromatography (RPC) and ion exchange chromatography (IEC). These and other chromatographic techniques are commonly used for purification of biological samples such as biological liquids, typically to either isolate one or more component(s) e.g. biomolecule(s) such as virus, present in the biological sample or to remove undesired components. Most commonly, separation/isolation of virus is effected by IEC using a matrix with ligands to which the specific virus has affinity. Suitable ligands for virus separation using IEC include sulfate ligands (S-ligands) and quaternary amine ligands (Q-ligands). For instance, influenza virus is typically separated/isolated by IEC using a matrix to which S-ligands are linked, whereas separation of adenovirus is performed using a Q-linked matrix, such as a cross-linked agarose matrix to which Q-ligands are linked either directly or via dextran extenders.

In addition to chromatographic separation methods, magnetic separation may be used for the separation/isolation of biomolecules. In this method, magnetic beads carrying the appropriate ligand are used. The desired biomolecule binds to the ligand and the separation is then effected by a magnetic field by using a magnetic separator.

Spherical agarose gel beads for use in chromatographic separation applications are typically obtained by methods based on phase separation including e.g. suspension gelation, spraying gelation etc. The basic process of these methods is that an aqueous agarose solution having an agarose concentration typically in the range of 4-6% w/v is dispersed into an organic phase by mechanical stirring or spraying. The droplets thus formed are then solidified upon cooling. Magnetic beads for use in magnetic separations, are typically prepared by adding a magnetic material to the aqueous agarose solution prior to dispersing it into the oil phase. In order to obtain more rigid beads that better will withstand the pressure often exerted in methods of column chromatography, the agarose gel is often cross-linked. The cross-linking is normally achieved by reacting the formed beads with a cross-linking agent.

Biological products are commonly used in many applications within the field of cell biology, and biochemical research and engineering. Biological products are for example used in drug development and many drugs today are so called biologics or biopharmaceuticals, i.e. pharmaceutical drug products manufactured in, extracted or semi-synthesized from biological sources such as blood, blood products, somatic cells, bacteria, virus, antibodies etc. In addition, biological products are frequently used in the field of virus vaccines wherein samples such as example lysates or serum containing the biological products serve as source for virus. Another example wherein biological products are used is the field of gene therapy, wherein viruses are used as carriers of genes intended for therapeutic applications. Among the methods commonly used for gene transfer, adenovirus-based vectors have proved particularly promising. Adenovirus is a non-enveloped DNA-virus with a diameter of about 90 nm which belongs to the family Adenoviridae. The family Adenoviridae consists of a large number of serotypes and several genera that can infect both animals and humans.

WO98/26048 relates to virus purification by anion exchange chromatography followed by size exclusion chromatography.

WO2006/052088 relates to a separation matrix of porous carbohydrate particles to which antibody-binding protein ligands have been immobilized. The matrix is suitable for purification of monoclonal antibodies.

WO2008/039136 relates a to separation matrix comprising an insoluble carrier to which sulfate ligands are attached via extenders. The disclosed matrix is suitable for the purification of virus, especially influenza virus.

WO97/38018 relates to a process for the production of a porous cross-linked polysaccharide gel in which a bifunctional cross-linking agent is introduced into the polysaccharide solution before emulsion and gel formation.

U.S. Pat. No. 6,537,793 relates to viral purification using a matrix chosen from agarose, dextran, acrylamide, silica and poly[styrene-divinylbenzene]. More particularly, the invention relates to a method of purifying and quantifying adenovirus by ion exchange chromatography. It is stated to be particularly advantageous to use a strong anion exchanger, particularly preferred is Q Sepharose XL which is an agarose base matrix to which Q-groups have been attached via dextran.

Prior art beads and chromatography matrixes for separation and/or isolation of biomolecules are typically optimized for the separation/isolation of particles having sizes in the range 5-10 nm e.g. biomolecules such as antibodies, proteins, nucleic acids, etc. Larger particles such as virus are typically isolated using beads to which specific virus interacting ligands have been attached. In some prior art beads, the ligands are attached via extenders. In these cases, the large (virus) particles essentially only bind to the external surfaces of the beads, with a resulting low binding capacity.

SUMMARY OF THE INVENTION

In one aspect, the present invention provides a method of preparing a porous cross-linked agarose gel beads comprising the steps of:

a) Emulsifying,
   (i) preparing an agarose aqueous phase having an agarose concentration of 0.3-0.8% w/v (W),
   (ib) optionally adding a magnetic material, such as magnetite,
   (ii) preparing a water-immiscible oil phase (O) in which at least one emulsifier is dissolved,
   (iii) mixing the water phase (W) and the oil phase (O) to obtain a W/O emulsion, (iv) allowing the W/O emulsion to form beads.
b) Cross-linking the emulsified agarose one or several times by reacting the beads with a cross-linking agent,
c) Optionally coupling of ligands.

In another aspect, the present invention relates to porous cross-linked agarose gel particles obtainable by the method disclosed above.

In a further aspect, the present invention relates to porous, spherical cross-linked agarose gel beads, having an agarose concentration of about 0.3-0.8% w/v or a dry weight of 5-15 mg/mL, and optionally comprising a magnetic material.

In a further aspect, the present invention relates to a separation matrix comprising porous, cross-linked agarose gel beads prepared according to the method described above.

In a further aspect, the present invention relates to a method of separating particles in a liquid from other components in the liquid comprising the steps of:
   a) contacting the liquid with the separation matrix as described above to allow adsorption and/or absorption of the particles,
   b) optionally washing the separation matrix,
   c) eluting the particles from the matrix by adding a liquid that releases the particles,
   d) recovering the particles from the eluate.

In a further aspect, the present invention relates to the use of porous cross-linked agarose gel beads as described above as a matrix in affinity chromatography, ion exchange chromatography, hydrophobic interaction chromatography, reversed phase chromatography, chelate chromatography, covalent chromatography, size exclusion chromatography.

The beads according to the invention are especially useful for the separation of large particles, such as particles having a size of about 20-400 nm. In particular, the beads are useful for the separation of virus particles, such as virus particles in a biological sample. The pores are large enough that the particles can interact with internal pore surfaces and the beads are sufficiently resilient for mechanical handling, particularly in batch adsorption processes where beads comprising magnetic material can be used.

DETAILED DESCRIPTION OF THE INVENTION

Definitions & Abbreviations

The term "biomolecule" as used herein means molecules that occur naturally in living organisms. Biomolecules include macromolecules like virus, proteins, carbohydrates, lipids and nucleic acids, as well as small molecules like primary and secondary metabolites and natural products.

The term "extender" as used herein means a molecule such as a polymer which is covalently linked to the agarose.

The term "ligand" as used herein in means a molecule which is capable of interacting with a target compound such as a biomolecule, e.g. a virus.

The terms "separation matrix" and "matrix" which are used interchangeable herein are meant to mean an insoluble carrier to which extenders and/or ligands may be attached.

The term "resin" as used herein means a separation matrix for use as chromatography medium. The resins, according to the present invention, are constituted of agarose gel beads.

The term "ion capacity" as used herein means the capacity of a matrix carrying ligands to bind an ion species. The ion capacity is normally determined by titration methods known in the art and is expressed as micromol or millimol/mL sedimented matrix.

The term "binding capacity" as used herein means the capacity of a matrix to bind a particle species, e.g. a virus particle.

In addition to the definitions above, the following abbreviations are used herein. If an abbreviation used herein is not defined it is meant to have its generally accepted meaning.
   DBC Dynamic binding capacity
   ECH Epichlorohydrin
   GMAC Glycidyl trimethylammoniun chloride
   VP Virus particle(s)

Most commonly, separation/isolation of adenovirus is effected by ion exchange chromatography using a matrix with Q-ligands. The Q-ligand is quite unselective since many other proteins typically occurring in raw virus feed also bind to it. Chromatographic methods using the Q-ligand thus does not provide pure adenovirus in a simple and efficient way, and repetitive and/or complementing purification steps may be required.

In view of the prior art there is in many aspects a need to separate/isolate particles such as biomolecules, for instance virus, from biological products, especially for use in the medical and diagnostic field. Improved methods providing increased capacity and more efficient separation and isolation of particles especially of large biomolecules are required, both in laboratory scale and for large-scale production.

Agarose gel beads for use in chromatography separation matrixes are usually equipped with ligands which are attached to the surface of the agarose, both to the outside surface of the beads and to the surface within the pores of the beads. During separation of particles in a liquid using such a matrix, the liquid is brought into contact with the matrix to enable the particles to adsorb to the ligands. Other components in the liquid which don't have affinity for the ligands will pass the matrix without adsorption and can easily be washed away. An important factor influencing the capacity of a matrix is the effective surface area of the beads available for adsorption of the particle, e.g. biomolecule, to be separated/isolated. The surface area depends on the pore size of the agarose gel beads in relation to the size of the particles, and thus, a way to improve the capacity of a matrix, is to use beads having a pore size large enough to enable the particles to enter into the pores. Preferably, the pore size of the beads is about twice the size of the particle to be separated.

Prior art beads for separation matrixes are typically optimized for the separation of smaller particles, i.e. particles having sizes in the range 5-10 nm e.g. biomolecules such as antibodies, proteins, nucleic acids, etc. When separating larger particles, for instance virus particles, from a biological sample e.g. a cell lysate, serum or the like, using prior art beads the available surface area for interaction with the particle to be isolated is thus restricted to the outside of the beads. As a consequence, the capacity of the beads for larger particles is considerably lower than for smaller particles and hence, larger amounts of beads, larger separation columns, larger amounts of solvents etc. will be required for their separation.

The pore size of the agarose beads formed in the preparation of an agarose gel depends on i.a. the content of agarose in the aqueous phase. A low agarose content provides beads with a larger pore size, and vice versa. It has been shown that the beads prepared according to the method of the present invention have pore sizes large enough to enable large particles, such as particles having a diameter of about 20-400 nm, to enter into the pores. Typical prior art agarose beads are prepared using an agarose content of about 4-6% w/v, thus providing beads suitable for filtration methods and/or separation of particles having sizes about 5-10 nm. Agarose beads prepared according to these prior art methods typically results in agarose beads having a particle size in the range 40-80 μm, whereas the agarose beads prepared according to the method of the present invention have sizes in the range 40-200 μm.

Accordingly, in one aspect the present invention provides a method for the preparation of porous cross-linked agarose beads comprising the steps of:
(a) Emulsifying,
  (i) preparing an agarose aqueous phase having an agarose concentration of 0.3-0.8% w/v (W),
  (ib) optionally adding magnetite,
  (ii) preparing a water-immiscible oil phase (O) in which at least one emulsifier is dissolved,
  (iii) mixing the water phase (W) and the oil phase (O) to obtain a W/O emulsion,
  (iv) allowing the W/O emulsion to form beads.
(b) Cross-linking the emulsified agarose one or several times by reacting the beads with a cross-linking agent,
(c) Optionally coupling of ligands.

More specifically, in step (a)(i), an agarose aqueous solution is prepared in a predetermined concentration. The solution obtained in step (a)(i) will constitute the aqueous phase and is denoted W. The agarose concentration in the aqueous phase is in the range between 0.1 and 1% w/v, such as in the range 0.3-0.8% w/v and more specifically in the range 0.4-0.6% w/v.

Agarose for use in the present invention is typically standard agarose but may also be any suitable derivative of agarose i.e. agarose which has been chemically modified. For instance, hydroxyethyl agarose, hydroxymethyl agarose or allyl agarose may be used. In these types of derivatised agarose, the number of intrastrand hydrogen bonds is reduced resulting in lower melting and gelling temperature than natural agarose. The exact temperatures are determined by the degree of substitution. These derivatised agaroses are commonly referred to as low-melting-point (LMP) agaroses. Some types of agaroses may gel only at 8-15° C. These types of agaroses are referred to as ultra-low melting or gelling temperature agaroses.

The agarose aqueous solution is prepared by mixing the appropriate amount of agarose in water while stirring. An elevated temperature is normally required to get the agarose in the water-agarose mixture into solution such as a temperature above the melting point of the agarose. The suitable temperature will depend on the type of agarose used and will typically be above 80° C. such as 90° C. or higher.

The method may also comprise the preparation of magnetic beads. In this case, the step (ib) is added to step a) of the method. In step (ib) a magnetic material such as magnetite particles is added to the aqueous phase obtained in step a)(i) prior to mixing the aqueous phase (W) with the oil phase (O). Specifically, the magnetic material may be added to the agarose and water mixture right after addition of the agarose. The concentration of the magnetic material is typically in the range 10 to 90 g/L agarose solution, such as 30 to 70 g/L agarose solution or 40 to 60 g/L agarose solution. Typically, the concentration of the magnetic material is 50 g/L agarose solution.

In step a)(ii) the water-immiscible oil phase (0) is prepared. In the oil phase, at least one oil-soluble and/or oil-dispersible emulsifier is dissolved/dispersed. Examples of suitable emulsifiers include ethyl cellulose, sorbitan esters such as ethoxylated sorbitan esters (Tween™), sorbitan sesquiolate (e.g. Arlacel™ 83), sorbitan trioleate (e.g. Span™ 85), sorbitan monooleate (e.g. Span™ 80), sorbitan tristearate (e.g. Span™ 65) polyglycerol esters such as hexaglycerol pentaoleate ester (PO-500, PO-310), polyethylene glycol hydrogenated castor oil, or lipophilic-hydrophilic block polymers. The emulsifier in the oil phase may e.g. have a concentration between 0.1 and 2.0% w/v, such as between 0.5 and 1.0% w/v, and the volume ratio of water phase to oil phase can be 2:1-1:100, such as 2:1-1:10 or 1:1-1:10.

In step a)(iii), an emulsion is obtained by mixing the water phase (W) and the oil phase (O). The mixing is typically effected by conventional mixing techniques such as using an overhead stirrer, or by way of static mixing. Prior to mixing the two phases, they are suitably brought to the same temperature. The suitable temperature of phases when mixing them is a temperature above the gelling point of the agarose used and thus, depends on the type of agarose used. Due to their lower gelling temperature, derivatised agaroses such as methyl, hydroxyethyl or allyl agarose are preferably mixed at lower temperature than natural agarose. For example, the water (W) and oil (O) phases are mixed at a temperature of about 40-70° C., such as 50 to 60° C. In the case of an ultra-low melting or gelling temperature agarose, the phases may be mixed at temperatures about 20-30° C.

In step a)(iv), W/O emulsion droplets are allowed to solidify i.e. to gel into agarose beads by cooling to a temperature below the gelling temperature. When beads of the desired size are obtained, the emulsion is allowed to attain the gelling temperature or lower. For native agarose, this can conveniently be 10-30° C. or room temperature, i.e. a temperature of about 20° C. For ultra-low gelling temperature agaroses, lower temperatures may be needed, e.g. 0-8° C.

In an alternative method, the beads are obtained by membrane emulsification. In this method, the dispersed phase obtained in step a)(iii) is forced through the pores of a microporous membrane. Emulsified droplets are thus formed and detached at the end of the pores with a drop-by-drop mechanism.

In a specific embodiment of the preparation method described above, step a) is specified as follows:
(i) the agarose aqueous phase (W) is prepared in a concentration of 0.4-0.6% w/v at a temperature above the melting point of agarose,
(iii) the water phase (W) and the oil phase (O) are mixed at a temperature of about 40-70° C., and
(iv) the W/O emulsion is allowed to attain a temperature below the gelling temperature, typically 10-30° C., such as about 20° C. and form particles.

High porosity beads, as the agarose beads disclosed herein, are generally soft and easily crushed. The strength of the beads can be improved by cross-linking the agarose. Accordingly, in order to obtain beads with improved physical stability as well as improved flow and packing and flow characteristics, that better will withstand the pressure often exerted during column chromatography, the method of the present invention comprises a step of cross-linking the agarose gel beads provided in step a). Thus, in step b) the emulsified agarose beads are cross-linked one or several times by reacting the beads with a cross-linking agent. The cross-linking is normally effected by reacting the formed beads with a cross-linking agent using methods and agents well known to a person skilled in the art. Suitable cross-linking agents are typically bifunctional compounds, i.e. a compound having two functional groups which can react with the hydroxyl groups of the agarose such as e.g. epichlorohydrin or a diepoxide. In an alternative approach, the cross-linking may be performed by reacting the agarose with a heterobifunctional reagent prior to the bead formation of step a)(iv), i.e. on the agarose in the W/O emulsion obtained in step a)(iii). A typical example is an allyl agarose solution obtained by reacting agarose in solution with an allyl halide or allyl glycidyl ether. The allyl groups can then, after emulsification and solidification of the beads, be used for crosslinking, e.g. by bromination to form reactive bromohydrins and/or epoxides capable of crosslinking reactions with hydroxyl groups in the agarose polymer.

In general, the cross-linking is effected by adding the cross-linking agent to a slurry of emulsified beads, optionally at an elevated temperature, and optionally in the presence of a base such as sodium hydroxide or similar. The suitable temperature for performing the cross-linking reaction will depend upon the cross-linking agent. In the case the cross-linking agent is epichlorohydrin, the cross-linking reaction is typically performed at a temperature in the range from 22 to 90° C., such as in the range from 30 to 60° C., and especially in the range from 45 to 55° C. The mixture is conveniently agitated to ensure substantially uniform distribution of the crosslinking agent. The cross-linking agent may be added in one portion but is preferably added in several portions spread during the reaction time. Usually, the reaction time will vary from about 4 to about 24 hours, especially from about 8 to about 20 hours such as about 12 to about 16 hours. When the reaction is deemed complete, the beads are washed with distilled or deionized water to remove any unreacted reagents and filtered. After the initial cross-linking step, additional cross-linking step(s) may be conducted if desired.

The cross-linking agent may e.g. be used in amounts of from 0.5 to 50 mmol, usually 1 to 25 mmol per gram of agarose.

In one embodiment of the invention, the cross-linking agent is epichlorohydrin

The method of the present invention comprises optionally an additional step in which ligands are coupled to the solidified agarose beads after step (b). The skilled person is well acquainted with methods for coupling of such ligands. Suitable ligands include charged groups such as quaternary amine ligands, sulphate ligands, virus affinity ligands, multimodal ligands. In a typical embodiment of the invention, the ligands are quaternary amine ligands. Particularly preferred quaternary amine ligands are Q-ligands, i.e. trialkylammonium ligands such as trimethylammonium ligands.

In one embodiment the method of the present invention comprises a step of grafting the agarose beads with extenders. The extenders are flexible, non-crosslinked polymers which are covalently linked to the agarose. The extenders may be comprised of polymers of synthetic or natural origin. In an illustrative method of grafting, the agarose gel is first activated, for example epoxy-activated by reaction with epichlorohydrin typically in the presence of a base such as NaOH or the like. The obtained activated agarose gel is then reacted with the extender typically in the presence of a base such as NaOH or the like and a reducing agent such as $NaBH_4$ or similar. The extender can typically be a soluble polysaccharide, e.g. dextran.

In one approach, the method described above comprises the additional step of grafting the bead obtained in step b) with extenders.

In an alternative approach, the method comprises attaching, in a first step, a ligand to the extenders and, in a subsequent step, grafting the bead obtained in step b) with the extender-ligand complex.

In yet another approach, functional monomers, e.g. charged monomers, may be graft polymerised onto the agarose gel, forming functional graft polymers extending from the agarose molecules.

In one aspect, the invention relates to porous cross-linked agarose gel beads obtainable by the method described above.

The low content of agarose used in the method of preparing the agarose beads according to the present invention compared to the agarose content used in prior art methods, provides beads having considerably larger pores then the pores in the beads obtained by prior art methods. It has been shown that the beads prepared according to the method of the present invention have pores large enough to enable large particles, such as particles having a size of about 20-400 nm, to enter. In addition to enabling large particles to enter into the pores, the large pore size of the beads prepared according to the method of the invention, the large pore size provides a larger surface area available for ligand coupling, which in turn increase the binding capacity of the beads.

The method of the present invention thus provides porous spherical cross-linked agarose gel beads useful for separation of particles, such as biomolecules from a liquid. The beads are particularly useful for the separation of particles having sizes of about 20 nm or more, such as 50 nm or more. As described above, the method provides beads having an agarose concentration in the range between 0.1 and 1% w/v, such as in the range 0.3-0.8% w/v and more specifically in the range 0.4-0.6% w/v. Accordingly, the present invention provides porous spherical cross-linked agarose gel beads, having an agarose concentration in the range between 0.1 and 1% w/v, such as in the range 0.3-0.8% w/v and more specifically in the range 0.4-0.6% w/v.

The beads obtained by the method of the present invention may have a dry weight in the range of about 5-15 mg/mL. The dry weight may vary and depends on a number of factors such as number of cross-linking cycles, presence/absence of extenders and presence/absence of magnetic material in the beads, where the dry weight increases with the number of crosslinking cycles performed and also with the presence of extenders and/or magnetic material. For example, the dry weight of beads which are cross-linked once, not grafted with extenders or ligands and not comprising magnetic material is typically in the lower end of the range, such as about 5-9 mg/mL, whereas the dry weight of beads which are cross-linked three times, are dextran grafted and don't comprise a magnetic material typically is in the higher range, such as about 9-15 mg/mL. Beads additionally comprising a magnetic material will typically have an even higher dry weight. The dry weight of the beads correlates to the bead's porosity where a low dry weight corresponds to a higher porosity and vice versa.

In general, a low dry weight of beads, such as the beads of the present invention, is expected to result in a lower ligand concentration since the low agarose content, entails a lower surface area available for ligand coupling. A low ligand concentration in turn is expected to provide a lower ion capacity of the beads. The ligand concentration of the beads of the invention was calculated and found to be surprisingly high. For example, for the bead 029271 (cross-linked once, coupled with Q-ligand and not dextran grafted), the ligand concentration was calculated to be 2700 µmol/g. This can be compared to the ligand concentration of the prior art resin MagSepharose, (4% agarose, grafted with dextran and coupled with Q-ligand) which is 977 µmol/g. The Q-coupled agarose beads of the present invention were thus found to have a considerably higher ligand concentration than would have been expected from prior art Q-coupled agarose beads.

The binding capacity of the beads of the present invention was investigated. The beads were coupled with Q-ligands and the binding capacity for viruses was measured as detailed in the experimental part hereinbelow. The beads of the present invention were found to outperform prior art beads of similar particle size in terms of binding capacity.

Accordingly, in one aspect, the present invention provides porous spherical cross-linked agarose gel beads, having an agarose concentration of about 0.3-0.8% w/v, or a dry weight of about 5-15 mg/mL, optionally comprising a magnetic material.

In one embodiment of the invention, the porous cross-linked agarose beads have a particle size of 40-200 µm. Advantageously, the particle size is in the range of about 50-150 µm, such as 80-120 µm.

In one embodiment, the invention provides porous cross-linked agarose gel beads to which ligands are attached.

Suitable ligands include charged groups such as quaternary amine ligands, sulphate ligands, virus affinity ligands, multimodal ligands.

In a typical embodiment of the invention, the ligands are quaternary amine ligands. Particularly preferred ligands are Q-ligands, i.e. trialkylammonium ligands such as trimethylammonium ligands.

In one embodiment, the invention provides porous cross-linked agarose gel beads to which ligands are attached via extenders. The extenders are advantageously flexible, non-crosslinked polymers, which provide a distance between the carrier and the ligands. The extenders may be comprised of polymers of synthetic or natural origin. Examples of natural polymers include dextran, starch and cellulose, and mixtures thereof. Advantageously, the extenders are dextran molecules. Such dextran extenders may be of a molecular weight in the range of 10-200 kDa, such as a molecular weight in the range of 20-140 kDa, advantageously in the range of about 50-90 kDa.

Alternatively, the extenders are synthetic polymers, such as polyacrylamide, polymethacrylamide or polyvinyl ether polymers, or any mixture thereof. The synthetic extenders may have molecular weights similar to those of the above-discussed dextran extenders.

As the agarose beads is a soft material, large pores may lead to a weakened structure of the beads making them vulnerable to the pressure, especially at high flow rates, in traditional column chromatography. An alternative separation method suitable for applications where large porous beads are desired is magnetic bead chromatography or magnetic bead batch adsorption. In short, the method uses magnetic beads typically equipped with ligands to which the biomolecule of interest is getting bound. The supernatant is then removed by simply pouring it away while keeping the magnetic beads with the captured biomolecule in place with an external magnetic field. The absence of pressure on the beads in this method makes it mild and gentle and thus suitable also for sensitive target molecules.

Magnetic beads are typically prepared using a procedure similar to the preparation procedure for non-magnetic beads. The magnetic material is normally incorporated in the beads during the emulsification step. As for non-magnetic beads, the magnetic beads are typically equipped with the suitable ligands, such as affinity ligands or ion exchange ligands. A procedure for the preparation of magnetic beads is detailed in the experimental part herein below. Suitable magnetic particles for use in the magnetic beads include e.g. magnetite. Accordingly, in one embodiment, the porous agarose gel beads further comprise magnetic particles, e.g. magnetite. Typically, according to this embodiment, the amount of the magnetic particle is 20-80 g/L agarose solution.

In one aspect, the present invention relates to a separation matrix comprising porous cross-linked agarose gel beads as defined above. Such a matrix is useful for the separation of a particle, such as a biomolecule, from other components in a liquid. In an advantageous embodiment, ligands are attached to the beads comprised in the separation matrix. The suitable ligand attached is as described hereinabove and is selected in accordance with the particle to be isolated.

In one aspect, the present invention relates to a method of separating at least one particle from other components in a liquid. The aim of the separation is either for the purification of the desired particle or to remove one or more particles from the liquid. Thus, in one embodiment, the method comprises contacting a liquid comprising said particle with a separation matrix. In an advantageous embodiment, the separation matrix is the matrix described above. The liquid from which said at least one particle is separated may be a culture liquid, wherein the particle has been produced, such as a fermentation broth or a cell culture supernatant. Alternatively, the liquid may be a biological liquid, such as blood, serum or the like originating from a human or animal. Such liquids may comprise various compounds from which it is desired to separate the particle of interest.

In one aspect, the present invention relates to a method of separating at least one particle in a liquid from other components in the liquid comprising the steps of:
  a) contacting the liquid with the separation matrix as described above to allow adsorption and/or absorption of the particle(s),
  b) optionally washing the separation matrix,
  c) eluting the particles from the matrix by adding a liquid that releases the particle(s),
  d) recovering the particle(s) from the eluate.

In one embodiment, the separation method further comprises the step of separating the liquid and the matrix from step a) by sedimentation, filtration, decantation or centrifugation, or in the case of magnetic beads, by a magnetic field.

Thus, according to the present invention, particles such as virus are separated from other, usually non-desired components in the liquid. The liquid may be a cell culture liquid wherein virus-producing cells have been cultured and the non-desired components in the liquid, are for instance host cell proteins, residues of nutrients, aggregates etc.

In one embodiment, the particle(s) separated by the methods described above is a virus. In a specific embodiment, the virus is an adenovirus.

The separation method according to the present invention may be used in purification protocols combined with other steps for particle separation. For example, separation/purification methods such as filtration and/or other chromatography methods may suitably be combined with the separation method of the present invention. The skilled person can easily define the appropriate steps and method(s) in such a purification protocol and the order of such steps.

In one aspect, the invention relates to the use of porous cross-linked agarose gel beads according as described above as a matrix in affinity chromatography, ion exchange chromatography, hydrophobic interaction chromatography, reversed phase chromatography, chelate chromatography, covalent chromatography.

EXPERIMENTAL

The agarose beads were prepared in three or four steps:
(a) emulsification of agarose solution, optionally with addition of magnetite,
(b-i) cross-linking,
(b-ii) dextran grafting, optional,
(c) ligand coupling.

Beads both with and without magnetite were prepared.
(a) Emulsification of Agarose Solution
Two Separate Solutions were Prepared:
(W) Agarose (0.5% w/v) was added to a round bottom flask containing distilled water. The mixture was stirred at about 200 rpm at a temperature above 90° C. When all agarose was dissolved, the temperature was lowered to 50-60° C.
(O) Ethyl cellulose N50 (Aqualon) was added while stirring at 150 rpm to an emulsification reactor containing toluene. The solution was heated to 50-60° C.

When all the ethyl cellulose N50 in solution (O) was dissolved, the agarose solution (W) was poured into the emulsification reactor during approximately 2 minutes. The rate of the stirrer was increased and samples for particle size measurement using a particle size distribution meter ("Mastersizer 2000", Metrohm) were taken every 15 minutes. After each sampling, the stirring rate was increased until the desired particle size was obtained (around 100 μm). The stirring rate was then lowered to about 225 rpm and the emulsion was cooled to 20° C. at a rate of 0.5° C./min. The emulsion was poured into a beaker with ethanol while stirring and the gel was left to sediment for 18 h. Liquid was decanted and new ethanol was added, this procedure was repeated four times. Then distilled water was added and decanted five times. The particle size distribution was measured and the gel was checked in microscope for damage.

The temperature and concentration of ethyl cellulose for the emulsification were varied between the experiments as indicated in Table 1.

The emulsification procedure of magnetite-containing agarose gels was as described for the non-magnetite gels complemented with addition of magnetite (<5μ, Aldrich) to the agarose-water mixture directly after addition of the agarose. The magnetite concentration was 50 g/L agarose solution.

(b-i) Cross-Linking
A slurry of emulsified beads with concentration of 75% was heated to 35° C. in a round bottom flask. 2.55 M $Na_2SO_4$ was added to the solution and dissolved for one hour. The temperature was increased to 90° C. (in one experiment to 50° C.) for one hour, then decreased to 47° C. with a rate of 1° C./min. 0.18 M NaOH (50%) was added together with $NaBH_4$ and then additional NaOH (50%) and epichlorohydrin (ECH) was added during a five-hour interval. The reaction went on for 14±2 hours. The obtained resin was washed with distilled water on a glass filter. For some of the prototypes, two additional cross-linking steps were performed. In the additional cross-linking steps, the conditions were the same as described for the first cross-linking step with the exception that the temperature did not exceed 50° C. and $NaBH_4$ was not added. The obtained resins were examined with SEC, dry weight measurements and visually in light microscope.

(b-ii) Dextran Grafting, Optional
A mixture of dextran (dextran T40, dextran 70 (Amersham Biosciences), dextran 110 (Pharmacosmos) in distilled water was stirred at 80 rpm in a round bottom flask until the dextran was dissolved.

In a separate flask, water was added to cross-linked resin from step b, previously washed in distilled water and drained. The mixture was stirred at 300 rpm and warmed in a water bath at 27° C. NaOH-pellets were added and the mixture was left until the NaOH was dissolved (~15 min). Epichlorohydrin (ECH) was added and the mixture was left for epoxy-activation for two hours and then washed with distilled water until neutral pH was obtained. The epoxy-activated resin was added to the dextran containing flask followed by addition of water and the mixture was stirred at 120 rpm. The flask was placed in a water bath at 40° C. and left for 20 minutes. $N_2$-gas was then bubbled into the solution while stirring for 20 minutes. NaOH (50%) and $NaBH_4$ was added to the slurry and the reaction was left for 18 hours. Distilled water was added and the resin was washed on a glass filter with distilled water.

(c) Ligand Coupling
The beads from step (b-i) or (b-ii) were washed with NaOH (4-8 M), transferred to a round bottom flask and either:
cooled on an ice-bath whereafter glycidyl trimethylammonium chloride (GMAC) was added in the amount as indicated in Table 1. The reaction mixture was kept on the ice bath for 10 min and then left at rt for 18±2 hours
or
$Na_2SO_4$ and GMAC were added at rt and after 10 min at rt the reaction mixture was heated to 35° C. and stirred at 35° C. for 18±2 hours.

The obtained resin was washed with distilled water.

A summary of the experimental parameters used in the preparation of agarose beads is presented in TABLE 1. All resins were cross-linked once unless otherwise indicated.

TABLE 1

| Sample | Volume ratio resin:GMAC | c(NaOH) [M] | X-link Temp [° C.] | c(Na₂SO₄) [M] | Dextran type [kDa] | Magnetite | Ion cap. [μmol/mL] |
|---|---|---|---|---|---|---|---|
| 029446[1] | 1:6 | 4 | 35 | 2 | — | No | na |
| 029509 "low" | 1:1.2 | 2 | rt | 0 | 40 | No | na |
| 029509 "high" | 1:6 | 4 | 35 | 2 | 40 | No | na |
| 029679 | 1:6 | 4 | 35 | 2 | 40 | Yes | na |
| 029799 | 1:6 | 4 | 35 | 2 | 70 | Yes | na |
| 029836 | 1:6 | 4 | 35 | 2 | 110 | Yes | na |
| 029106 | 1:3 | 4 | rt | 0 | — | No | 6.0 |
| 029113[2] | 1:3 | 4 | rt | 0 | — | No | 3.5 |

TABLE 1-continued

| Sample | Volume ratio resin:GMAC | c(NaOH) [M] | X-link Temp [° C.] | c(Na$_2$SO$_4$) [M] | Dextran type [kDa] | Magnetite | Ion cap. [μmol/mL] |
|---|---|---|---|---|---|---|---|
| 029195 | 1:3 | 4 | 35 | 0 | — | No | 3.2 |
| 029181 | 1:3 | 4 | 35 | 1 | — | No | 6.25 |
| 029219 | 1:3 | 8 | 35 | 1 | — | No | 8.75 |
| 029189 | 1:6 | 8 | 35 | 1 | — | No | 8.32 |
| 029220 | 1:6 | 4 | 35 | 1 | — | No | 9.15 |
| 029271 | 1:6 | 4 | 35 | 2 | — | No | 17.42 |
| 029309 | 1:6 | 4 | 35 | 2.55 | — | No | 16.55 |
| 029335[2] | 1:6 | 4 | 35 | 2 | — | No | 11.97 |

[1]Cross-linked 5 times
[2]Cross-linked 3 times
na = not addressed

Determination of Dry Weight of the Agarose Beads (Non-Magnetite Beads)

A slurry of agarose beads was properly stirred then transferred to a 1 mL Teflon cube using a plastic pasteur pipette. Vacuum was applied (−0.8 to −0.9 bar) and when the resin surface was dry, the sample was left under vacuum for additional 20 seconds. The cube was split under vacuum and the 1 mL resin plug was transferred to a glass filter and washed with acetone. The sample was dried in an oven at 105° C. over night and then placed under vacuum in a desiccator for one hour before the samples was weighed. The results are shown in TABLE 2.

TABLE 2

| Number of cross-linking cycles | Dry weight [mg/mL] | | |
|---|---|---|---|
| | Cross-linked | Epoxy activated | Dextran grafted |
| 1 | 6.45 | 7.0 | 9.55 |
| 3 | 9.45 | 10.15 | 11.6 |

Estimation of Pore Size

The pore size of beads prepared were analysed by inverse SEC of NaCl and four different dextran types, i.e. particles with significant different sizes.

A slurry of beads having an agarose content of 0.5% and being cross-linked once was poured into a 24 mL HR10/30 column (GE Healthcare) with an additional column packing tube attached to the top. The tubes were sealed in both ends and a 0.2 M NaCl buffer was flowed through the column. The additional packing tube was removed and replaced by an adapter unit and a filter. Prior to starting the chromatography, the column was subjected to an asymmetry test to make sure it was correctly packed and that eluted peaks were symmetric. The SEC was performed by HPLC (ÄKTA™ explorer, GE Healthcare) and the retention volume of each of the samples was measured by a refractive index instrument.

The analysis showed no significant difference in elution volume between the particles, which indicates that the beads have pores large enough to allow entrance of large particles and hence is suitable for virus and macromolecule applications. The result is summarized in TABLE 3.

TABLE 3

| Particle | Elution volume [mL] |
|---|---|
| NaCl | 24.6 |
| 196k dextran | 24.17 |
| 1 million dextran | 22.35 |
| 3 million dextran | 21.12 |
| Native dextran | 18.02-20.55 |

Three different beads prepared according to the present invention were used as matrix in SEC of adenovirus to investigate the impact of cross-linking and of presence of magnetic material in the beads. The tested beads were not dextran grafted and had no ligands attached. The SEC was performed on a HPLC-system (1290 Infinity) from Agilent technologies using a 0.2 M NaCl solution with 80% 20 mM Tris buffer as mobile phase. The result is summarized in Table 4

TABLE 4

| Bead # | Cross-linked | Magnetite | Ret. time [min] | Flow [mL/min] | Elution volume [mL] | Column volume [mL] |
|---|---|---|---|---|---|---|
| 1 | x1 | No | 247 | 0.08 | 19.8 | 23.1 |
| 2 | x3 | No | 245 | 0.1 | 24.5 | 23.4 |
| 3 | x1 | Yes | 264 | 0.09 | 23.8 | 22.7 |

No significant differences in elution volume between the beads were found, indicating that cross-linking and presence of magnetic material have no significant impact on the pore size of the beads.

To investigate if the interactions between resin and adenovirus are only ionic interactions, size exclusion chromatography of adenovirus was performed using two different salt concentrations of the buffer, one with 0.2 M NaCl and one with 0.4 M NaCl. A magnetite containing resin which was cross-linked once, not dextran grafted and not ligand coupled was used. The flow was 0.09 mL/min and the column volume was 22.7 mL. The results are summarized in TABLE 5.

| Salt conc. [M] | Elution volume [mL] |
|---|---|
| 0.2 | 23.8 |
| 0.4 | 23.5 |

If there were only ionic interactions between the adenovirus and the resin, the elution volume would have changed when changing the ionic strength of the buffer. This was found not to be the case, in fact, the elution volume remained in large the same when doubling the ionic strength of the buffer. It could thus be concluded that the interactions between resin and adenovirus are not only ionic interactions.

Assessment of Q-Ligands Density

The amount of Q-ligands coupled to the beads prepared was assessed by measuring the ion capacity of a resin consisting of Q-coupled agarose beads according to the invention.

The resin was washed with eight resin volumes 0.5 M HCl followed by 16 resin volumes of 1 mM HCl. Drained resin (1 mL) was transferred to a plastic cup equipped with a chloride ion-selective electrode. A solution of polyvinyl alcohol in Milli-Q water (6 mL, 0.2% w/w) was added so the electrode was covered with liquid. The mixture was stirred and a predetermined amount of 0.1 M $AgNO_3$ (10 mL, excess) was titrated into the solution while measuring the chloride potential. As silver ions were added, an AgCl precipitate was formed. When the entire volume of $AgNO_3$ was added, the titration stopped and the chloride potential was determined. The chloride potential correlates to the concentration of Q-ligands coupled to the beads. A 905 Titrando and a 800 Dosino from Metrohm were used for the measurement. The result of the assessment is summarized in TABLE 1.

As can be concluded from TABLE 1, the highest ion capacity was obtained for beads in which the agarose is cross-linked once, and have a ratio resin:GMAC of 1:6 (v/v). Additionally, the concentration of sodium sulfate was found to have a major impact on the resulting ion capacity of the resin.

Binding Capacities

The binding capacity of adenovirus of the resins prepared was evaluated in a batch adsorption test. Six different beads were tested.

1) A virus feed was prepared by diluting a sample of purified adenovirus with 20 mM Tris pH 8.0 buffer containing 300 mM NaCl to a concentration of 6.4× $10^{10}$ VP/mL. The obtained virus feed was kept at −70° C.
2) A slurry of 25% bead/resin was pipetted in different volumes into Eppendorf tubes. Non-magnetic beads were thereafter centrifuged for one minute with a relative centrifugal force of 7800×g, and magnetic beads were trapped using a mag-rack. Excess liquid was removed by pipetting.
3) Virus feed (1 mL) was added to each Eppendorf tube and the mixtures were incubated for one hour while mixed on a shaking table. The mixtures were then centrifuged and the supernatant (200 μL) was analysed by HPLC (Tricorn 550 column equipped with a coarse filter kit and packed with Q Sepharose XL™ resin). The equilibrium concentration $c^*$, i.e. number of virus remaining in the supernatant, was determined by UV detection. The concentration of virus particles is denoted herein as virus particles per volume (VP/mL). The concentration in the crude virus feed ($c_0$) was determined by quantitative polymerase chain reaction (qPCR).

The binding capacity $Q_{max}$ for each type of bead was calculated using equations (1) and (2) below $$c_0 \times V_{batch} c^* \times V_{batch} = Q^* \times m_p \quad (1)$$

$$Q^* = (Q_{max} \times c^*)/(K_d + c^*) \quad (2)$$

wherein
$c_0$ is the initial concentration of biomolecule,
$c^*$ is the equilibrium concentration of the biomolecule,
$V_{batch}$ is the volume of the biosuspension,
$Q^*$ is the equilibrium loading of the beads,
$m_p$ is the particle mass, and
$K_d$ is the dissociation constant of the resin.

A comparative study of the dynamic binding capacity of adenovirus of two resins according to the present invention and a prior art resin was performed. The resins were packed in columns and loaded with adenovirus sample beyond the breakthrough point. The chromatography conditions used were as follows:
Sample: adenovirus concentrated and diafiltered to 20 mM tris pH 8, with 300 mM NaCl added
Buffer: 20 mM tris pH 8+300 mM NaCl
Residence time: 10 min
Flow: 0.2 mL/min
Fractions of 0.5 mL were collected and analysed by HPLC using a NaCl gradient on Q Sepharose XL, to determine when the breakthrough occurred. The binding capacity was calculated as the total amount of virus particles loaded at the breakthrough point (vp), divided by the column bed volume (mL).

The result is summarized in TABLE 6.

TABLE 6

| Prototype | Binding capacity (vp/mL) |
|---|---|
| LS-026868 | 5.67E+11 |
| LS-026837 | 5.04E+11 |
| Capto Q (prior art) | 3.78E+11 |

The invention claimed is:

1. Porous spherical cross-linked agarose gel beads, comprising an agarose concentration of about 0.3-0.8% w/v, or a dry weight of about 5-15 mg/mL;
   wherein ligands are attached to the beads, the ligands being quaternary amine ligands, sulphate ligands, virus affinity ligands and/or multimodal ligands.
2. The porous cross-linked agarose gel beads according to claim 1, having a size of 40-200 μm.
3. The porous cross-linked agarose gel beads according claim 1, wherein the ligands are quaternary amine ligands.
4. The porous cross-linked agarose gel beads according to claim 1, wherein the ligands are attached via extenders.
5. The porous cross-linked agarose gel beads according to claim 4, wherein the extenders are carbohydrate molecules.
6. A separation matrix comprising porous cross-linked agarose gel beads as defined in claim 1.

* * * * *